United States Patent
Khan et al.

(10) Patent No.: US 11,104,954 B2
(45) Date of Patent: Aug. 31, 2021

(54) PLASMA DERIVED CELL-FREE MITOCHONDRIAL DEOXYRIBONUCLEIC ACID

(71) Applicant: UTI LIMITED PARTNERSHIP, Calgary (CA)

(72) Inventors: Aneal Khan, Calgary (CA); Christopher Newell, Calgary (CA); Stacey Hume, Edmonton (CA); Steven Greenway, Calgary (CA)

(73) Assignees: M.A.G.I.C. Clinic Ltd., Calgary (CA); The Governors of the University of Alberta, Alberta (CA)

( * ) Notice: Subject to any disclaimer, the term of this patent is extended or adjusted under 35 U.S.C. 154(b) by 246 days.

(21) Appl. No.: 16/090,394

(22) PCT Filed: Mar. 31, 2017

(86) PCT No.: PCT/CA2017/050405
§ 371 (c)(1),
(2) Date: Oct. 1, 2018

(87) PCT Pub. No.: WO2017/165982
PCT Pub. Date: Oct. 5, 2017

(65) Prior Publication Data
US 2019/0112661 A1    Apr. 18, 2019

Related U.S. Application Data (60) Provisional application No. 62/317,170, filed on Apr. 1, 2016.

(51) Int. Cl.
*C12Q 1/6883* (2018.01)
*C12Q 1/68* (2018.01)
*C12N 15/10* (2006.01)

(52) U.S. Cl.
CPC .......... *C12Q 1/6883* (2013.01); *C12N 15/10* (2013.01); *C12Q 1/68* (2013.01)

(58) Field of Classification Search
CPC .......... C12Q 1/6883; C12Q 1/68; C12N 15/10
See application file for complete search history.

(56) References Cited

U.S. PATENT DOCUMENTS

2014/0099648 A1\* 4/2014 Walker ................. C12Q 1/6883
435/6.12

FOREIGN PATENT DOCUMENTS

| CN | 101270390 B | 7/2011 |
|---|---|---|
| CN | 105087767 A | 11/2015 |

OTHER PUBLICATIONS

Lukomska et al., Stem Cells International, 2019(ID 9628536): 1-10, Apr. 2019.\*
Li et al., Bioscience Reports, 39 (BSR20182417): 1-9, May 2019.\*
Taylor and Turnbull, Nat. Rev. Genet., 65(5):389-402, May 2005.\*
International Preliminary Report on Patentability for International (PCT) Patent Application No. PCT/CA2017/050405, dated Oct. 11, 2018, 8 pages.
International Search Report and Written Opinion prepared by the Canadian Intellectual Property Office dated Jun. 7, 2017, for International Application No. PCT/CA2017/050405.
De Vlaminck et al. "Circulating Cell-Free DNA Enables Noninvasive Diagnosis of Heart Transplant Rejection," Science Translational Medicine, Jun. 2014, vol. 6, No. 241, 19 pages.
Evans et al. "Mitochondrial DNA genotypes in nuclear transfer-derived cloned sheep," Nature Genetics, Sep. 1999, vol. 23, No. 1, pp. 90-93.
Gordon et al. "An Algorithm Measuring Donor Cell-Free DNA in Plasma of Cellular and Solid Organ Transplant Recipients That Does Not Require Donor or Recipient Genotyping," Frontiers in Cardiovascular Medicine, Sep. 22, 2016, vol. 3, No. 33, 10 pages.
Hidestrand et al. "Highly Sensitive Non-Invasive Cardiac Transplant Rejection Monitoring Using Targeted Quantification of Donor Specific Cell Free DNA," Journal of the American College of Cardiology, Apr. 2014, vol. 63, No. 12, pp. 1224-1226.
Liu et al. "Circulating cell-free mitochondrial deoxyribonucleic acid is increased in coronary heart disease patients with diabetes mellitus," Journal of Diabetes Investigation, Jan. 2016, vol. 7, No. 1, pp. 109-114.
Xia et al. "Simultaneous quantitative assessment of circulating cell-free mitochondrial and nuclear DNA by multiplex real-time PCR," Genetics and Molecular Biology, 2009, vol. 32, No. 1, pp. 20-24.
European Search Report & Provisional Opinion in EP Application No. 17772917.5 dated Sep. 4, 2019.
Extended European Search Report & Opinion in EP Application No. 17772917.5 dated Dec. 17, 2019.
Human mtDNA Genome for Illumina Sequencing Platform; https://support.illumina.com/content/dam/illumina-support/documents/documentation/chemistry_documentation/samplepreps_legacy/human-mtdna-genome-guide-15037958-01.pdf. Feb. 1, 2016.
European Patent Office Communication in EP EP Application No. 17772917.5 dated Sep. 4, 2020.

\* cited by examiner

*Primary Examiner* — Cynthia B Wilder
(74) *Attorney, Agent, or Firm* — Hicks & Associates; Mark P. Roach (57) ABSTRACT

The present disclosure relates to a method for isolating and amplifying a subject's mitochondrial deoxyribonucleic acid (mtDNA). The method comprises the steps of: isolating cell free deoxyribonucleic acid (cf-DNA) from a plasma sample obtained from the subject; and amplifying the mtDNA within the isolated cfDNA using a polymerase chain reaction with a first primer pair and a second primer pair. The first primer is selected from SEQ ID NO: 1 and SEQ ID NO: 2 and the second primer pair is selected from SEQ ID NO: 3 and SEQ ID NO: 4.

13 Claims, 5 Drawing Sheets

Specification includes a Sequence Listing.

PLASMA DERIVED CELL-FREE MITOCHONDRIAL DEOXYRIBONUCLEIC ACID

CROSS-REFERENCE TO RELATED APPLICATIONS

This application is a national stage application under 35 U.S.C. § 371 and claims the benefit of PCT Application No. PCT/CA2017/050405 having an international filing date of 31 Mar. 2017, which designated the United States, which PCT application claimed the benefit of U.S. Provisional Application No. 62/317,170, filed on 1 Apr. 2016, the entire disclosures of each of which are incorporated herein by reference.

REFERENCE TO SEQUENCE LISTING

This application contains a Sequence Listing submitted as an electronic text file named "01-A8136992WO_ST25.txt", having a size in bytes of 1 KB, and created on 31 Mar. 2017. The information contained in this electronic file is hereby incorporated by reference in its entirety pursuant to 37 CFR § 1.52(e)(5).

TECHNICAL FIELD

This disclosure generally relates to a method and a tool for determining disease status or a haplotype of a subject. In particular, the disclosure relates to a method and a tool that isolate cell-free mitochondrial deoxyribonucleic acid (cf-mtDNA).

BACKGROUND

Mitochondria are cellular organelles that are responsible for a large portion of energy production within cells. Mitochondria produce energy in the form of adenosine triphosphate (ATP) via oxidative phosphorylation. The number of mitochondria present in a given cell depends upon the metabolic requirements of that cell. For example, a single cell may have a single large mitochondrion or thousands of mitochondria. Each mitochondrion contains dozens of copies of a subject's mitochondrial genome.

The mitochondrial genome is different from the nuclear genome in various respects. For example, the mitochondrial genome: is much smaller (17 Kb versus 3.2 Mb); exists in a circular, double-stranded form; has a higher error-rate; is synthesized by only a single enzyme (polymerase gamma); and it lacks histones. The mitochondrial genome is made up of mitochondrial deoxyribonucleic acid (mtDNA) and it contains about 37 genes. Functional proteins in the mitochondria can be encoded by either nuclear DNA (nDNA) or mtDNA. Genes encoded by nDNA are synthesized in ribosomes within the cytoplasm and then are imported into the mitochondria. It is widely considered that about 80% of mitochondrial disease is caused by mutations in nDNA and about 20% by mutations in mtDNA.

As with nDNA, mutations of mtDNA can arise by any number of causes including but not limited to: exposure to environmental mutagens; mtDNA replication errors; failure of cellular machinery that repairs mtDNA; defects in the mechanisms that degrade damaged mtDNA; and oxidative damage. The majority of mitochondrial diseases involve a deletion of some length from the mitochondrial genome.

Deletions of mtDNA play an important role in human pathology. Single mtDNA deletions are considered to occur when an identical mtDNA deletion is found in all cells within an affected tissue. Single mtDNA deletions are a common cause of sporadic mitochondrial disease. Multiple mtDNA deletions are primarily due to disrupted mitochondrial nucleotide-metabolism or disrupted mtDNA maintenance. Multiple mtDNA deletions can also be found in affected tissues, particularly in the muscle and the central nervous system. Deletions of mtDNA are also known to occur in aged post-mitotic tissues and in individuals with neurodegenerative diseases.

Mitochondrial disease encompasses a group of genetic disorders which affect approximately 1 in 5000 individuals. The same techniques may be used for detecting and analyzing mutations in nDNA in various genes such as those that cause sickle cell anemia, cystic fibrosis and virtually all other inherited diseases. These tests typically isolate nDNA from peripheral blood leucocytes for analysis. For at least three reasons mutations within mtDNA may pose problems for detection and analysis using peripheral blood leucocytes.

First, the mutation load of mtDNA can be variable with only a portion of the mtDNA having the mutation since there are many copies of mtDNA within a cell compared to the standard diploid arrangement of the nuclear genome. A small mutation load may be beyond the limits of detection for standard techniques that are used to test for mutations in nDNA.

Second, peripheral blood leukocytes can have a lower proportion of mutated mtDNA compared to their progenitor cells in the bone marrow. The reason is the progenitor cells require maturation into circulating cells and cells with mitochondrial mutations have lower survival. Therefore, for diagnostic purposes, the concentration of mutated mtDNA may be below the threshold of detection in some individuals and a peripheral leucocyte-derived DNA sample may generate a false negative.

Thirdly, if an mtDNA mutation is found in DNA isolated from the leukocytes, it is likely to represent only one tissue type (leukocytes) and may not represent the disease if it is affecting other tissues such as muscle, liver, heart etc.

On this basis, clinical testing for mitochondrial disease is a laborious task that typically involves several different clinical tests. For example, typical clinical tests for assessing a subject for mitochondrial disease may involve one or more of: a muscle biopsy; a skin biopsy; a blood draw; urine collection; and a buccal swab. These typical clinical tests can take one or more months to provide useful data for diagnosis. Furthermore, muscle and skin biopsies are invasive and can be painful for the subject and still only represent one tissue source.

SUMMARY

Cell-free DNA (cfDNA) is a form of DNA found within the circulatory system. During cellular apoptosis and general cell turn-over, small fragments of about 200 base pairs of mtDNA and nDNA are released from all cell types and persist in the circulatory system as cfDNA. Because cf-mtDNA is derived from all cell types, and without being bound by any particular theory, the inventors postulate that cf-mtDNA can be used to detect mutations in mtDNA from all tissue sources. Currently, cfDNA is used as a clinical biomarker in various fields including but not limited to: cancer biology and organ transplantation. Due to the presence of cfDNA in the circulatory system, a simple and non-invasive blood draw can provide the sample required for mtDNA analysis.

Various protocols are known for amplifying regions of mtDNA from plasma or serum using commercially available kits. According to the present disclosure, the isolated mtDNA is taken from plasma-derived cfDNA and the cf-mtDNA is then amplified by polymerase chain reaction (PCR) using primers that bind to sequences of interest within the mitochondrial genome. In one example, the sequences of interest are from overlapping sections of the mitochondrial genome.

One embodiment of the present disclosure relates to a method for isolating circular mtDNA from cfDNA samples, referred to herein as cell-free mtDNA (cf-mtDNA) and amplifying the circular mtDNA using two linear primers that are overlapping fragments of linear DNA that cover the entire mitochondrial genome.

Another embodiment of the present disclosure relates to a tool for isolating and amplifying circular mtDNA from a sample of cf-mtDNA taken from a peripheral blood-sample. The amplified circular mtDNA may be used for diagnosing one or more mitochondrial diseases or for other applications such as haplotyping.

Another embodiment of the present disclosure relates to use of fully intact, circular cf-mtDNA that is isolated from a subject's peripheral blood as a diagnostic screen for mitochondrial disease and haplotyping.

Another embodiment of the present disclosure relates to a method for isolating and amplifying a subject's mitochondrial deoxyribonucleic acid (mtDNA). The method comprises the steps of: providing a plasma sample obtained from the subject; isolating cell free deoxyribonucleic acid (cfDNA) from the plasma sample; and amplifying the mtDNA within the isolated cfDNA using a polymerase chain reaction with a first primer and a second primer. The first primer is selected from SEQ ID NO: 1, SEQ ID NO: 2, or both and the second primer is selected from SEQ ID NO: 3, SEQ ID NO: 4, or both.

BRIEF DESCRIPTION OF THE DRAWINGS

These and other features of the present disclosure will become more apparent in the following detailed description in which reference is made to the appended drawings.

DETAILED DESCRIPTION

The present disclosure relates to use of circular, cell-free, mitochondrial deoxyribonucleic acid (cf-mtDNA) that is collected, isolated and amplified from a subject's peripheral blood sample. The cf-mtDNA can be amplified and then sequenced for various applications including but not limited to detecting mutations in a subject's mtDNA, haplotyping or assessing mitochondrial transfer during a cell-administration therapy.

Definitions

Unless defined otherwise, all technical and scientific terms used herein have the same meaning as commonly understood by one of ordinary skill in the art to which this disclosure belongs.

As used herein, the term "about" refers to an approximately +/−10% variation from a given value. It is to be understood that such a variation is always included in any given value provided herein, whether or not it is specifically referred to.

As used herein, the term "blood" means a subject's blood that can flow through the subject's circulatory system and comprises red blood cells, immune cells, cellular waste materials, dissolved gases, proteins such as clotting proteins and various other components.

As used herein, the term "cell" means a single cell as well as a plurality of cells or a population of cells.

As used herein, the term "cell free" means substantially free of intact and viable cells. For example, a cell-free sample of blood obtained from a subject will have about 50% to about 100% less intact and viable cells than a sample of blood obtained from the same subject that is not cell free.

As used herein, the term "haplotype" and "haplogroup" mean the historical lineage of the mitochondrial genome over time as humans have moved from region to region across the globe. These phylogenetic differences can be mapped back to the mitochondrial genome for identification purposes by a process referred to herein as "haplotyping".

As used herein, the term "patient" means both human and veterinary subjects that are afflicted with a disease or disorder.

As used herein, term "plasma" means a liquid component of a subject's blood that is cell free and contains one or more proteins including clotting proteins. Plasma has not undergone a clotting process.

As used herein, the term "serum" means a liquid component of a subject's blood that is cell free, may contain one or more proteins and that is isolated from plasma or blood following a clotting process.

As used herein, the term "subject" means any vertebrate, for example, a mammal. Thus, the subject can be a human. The term does not denote a particular age or sex. Thus, adult, juvenile, and newborn subjects, whether male or female, are intended to be covered.

One embodiment of the present disclosure relates to a method for isolating mtDNA from a blood sample of a subject. The method comprises the following steps: Withdrawal of about 3 to about 5 mL of venous blood from a subject's peripheral vein using standard phlebotomy techniques. The blood was collected in tubes specific for isolating cell-free DNA (cfDNA) for example a CELL-FREE DNA BCT® tube (CELL-FREE DNA BCT is a registered trademark of Streck Inc., La Vista, Nebr., USA). The blood was processed, for example by centrifugation, to separate the plasma and the plasma component was stored for subsequent cfDNA isolation. Optionally, the plasma samples can be frozen and stored in a freezer. The cfDNA within the stored plasma samples was isolated using a commercially available kit. For example, the QIAAMP® Circulating Nucleic Acid Kit may be useful to isolate cfDNA (QIAAMP® is a registered trademark of the Qiagen Gmbh Corporation, Hilden, Federal Republic of Germany).

The isolated cfDNA was then quantified. While various DNA quantification techniques are suitable, the inventors used a QUBIT® 2.0 fluorometer and a concentration-response curve was generated (QUBIT is a registered trademark of Molecular Probes, Inc., Eugene, Oreg., USA). The QUBIT® 2.0 fluorometer measures the output of a fluorescent dye that preferentially adheres to molecules of DNA. This approach may provide an accurate estimate of the DNA content within a sample. Furthermore, because very small quantities of isolated cfDNA are in each sample, this approach provides a robust assessment of how successful the cfDNA isolation was.

Within the isolated cfDNA the entire circular mitochondrial genome was amplified. One example method of amplification that the inventors used was PCR with a first primer and a second primer. Typical PCR reactions amplify a product that will be hundreds or perhaps a thousand base pairs in length. Since the whole mitochondrial genome is 17,000 base pairs (17 Kb) the inventors developed the two primer pairs to select regions of interest, such as two overlapping sections to establish whether or not the full circular mitochondrial genome was present in the cfDNA that was isolated. This analysis allowed the inventors to determine the impact of deletions within the mtDNA and determine if the cfDNA only contained fragments of mtDNA.

Because cfDNA is a representative of all tissues within the body, detecting the circular mitochondrial genome may validate using cfDNA as a biomarker for mitochondrial mtDNA mutation load. Without being bound by any particular theory, the inventors hypothesized that the circular nature of the mitochondrial genome may play a role in protecting the cf-mtDNA from degradation.

Figure 1:
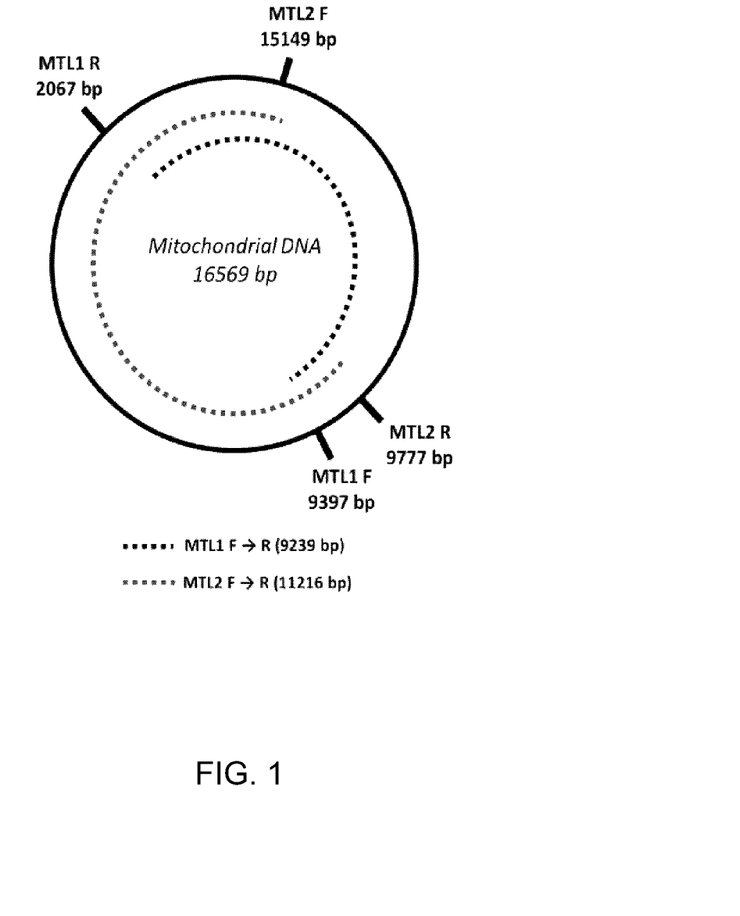
FIG. 1 is a schematic drawing of an example mitochondrial genome and two regions of interest.

The two different primer pairs are provided for recognizing two distinct overlapping regions of the mitochondrial genome (see FIG. 1). One primer pair is referred to as MTL1 and the other is referred to as MTL2. Table 1 below provides the primer sequence for these four primers.

TABLE 1

Description of the primer pairs generated to amplify two overlapping fragments of the whole intact circular mitochondrial genome.

| PCR Product | Primer Name | Primer Sequence 5' - 3' |
| --- | --- | --- |
| MTL1 (9239 bp) | MTL1 Forward* | SEQ ID 1:<br>AAAGCACATACCAAGGCCAC |
|  | MTL1 Reverse | SEQ ID 2:<br>GGTTCTGTGGGCAAATTTAAAG |
| MTL2 (11216 bp) | MTL2 Forward | SEQ ID 3:<br>TGAGGCCAAATATCATTCTGAG |
|  | MTL2 Reverse* | SEQ ID 4:<br>AATGTTGAGCCGTAGATGCC |

*These two primer sequences were obtained from the Illumina document "Human mtDNA Genome for the Illumina Sequencing Platform, rev.B" part no. 15037958.

These two primer pairs were selected specifically to amplify the entire mitochondrial genome in two overlapping fragments. These amplified sequences are then free to be quantified and pooled in equal quantities for subsequent sequencing and to examine the entire mitochondrial genome. The MTL1 and MTL2 were experimentally tested in approximately 50 patients and it has been determined that there are no single nucleotide polymorphisms (SNPs) spanning any of the MTL1 (forward/reverse) or MTL2 (forward/reverse) primers. This enables experimenting with lower or no concern about a common mutation within these regions of interest, which would lead to an inability to amplify these regions of interest. In other words, the mtDNA from a cfDNA sample from any subject can be amplified regardless of variations in the subject's haplogroup.

The PCR products were then separated on an agarose gel to determine if the full circular mitochondrial genome was present in the cfDNA samples following PCR amplification. Due to the size of the fragments examined the inventors used a two percent agarose gel (2%). A 2% gel was used because during optimization of the 1% gels there was consistent melting of the gel due to the voltage and length of time required to pull such large PCR products through the lower percentage gel. By increasing the gel percentage, thus increasing the amount of agarose, the gel was far less likely to melt when run at a high voltage (160 V) and when separating very large fragments for an extended period of time (e.g. over 2 hours). Because the two PCR primer pairs amplified products are of different lengths, the different sized products could be distinguished from each other and identified by the distance traveled through the gel. Seven samples (CN1 through CN7) were prepared from varying amounts of plasma and, hence varying amounts of cfDNA. These seven samples were run on a gel. The results demonstrated a substantially linear response of increasing band intensity for the samples that had higher amounts of cfDNA (see FIG. 3). The bands also persist at the same molecular weight across various samples for both primer pairs that were examined.

The PCR products were then sequenced. In order to identify specific differences between different cfDNA samples, Next-Generation Sequencing was performed using the MISEQ® platform (MISEQ is a registered trademark of Illumina, Inc., San Diego, Calif., USA). Individual nucleotide differences were examined following sample preparation using the NEBNEXT® Ultra II DNA Library Prep Kit available from Illumina, Inc. (NEBNEXT is a registered trademark of New England Biolabs, Inc., Ipswitch, Mass., USA). Output from the sequencing was examined using the free open-source software HaploGrep v2.0. This software compares input data to a comprehensive worldwide dataset to assess differences in the mtDNA corresponding to genetic variations accumulated over the course of human evolution and migration across the globe. The output is based on the well documented phylogenetic stability of mtDNA polymorphisms (single nucleotide changes).

The next steps involved sequencing of the amplified cf-mtDNA samples obtained from using the primer pairs MTL1 and MTL2 in PCR to detect other types of mutations specific to the mitochondrial genome. The use of the PCR amplified samples for sequencing could increase the coverage of the mitochondrial genome for subsequent haplogroup analysis—which could increase the specificity and sensitivity of this measurement. Ultimately, identifying mutations apart from those corresponding to a subject's haplogroup may allow an assessment of the subject's mitochondrial disease load using the same non-invasive blood draw described above.

Embodiments of the present disclosure relate to stem cell therapies for mitochondrial diseases by serving as a method to measure donor mtDNA in the recipient and possible "mitochondrial engraftment".

EXAMPLES

Example 1

One example of the present disclosure relates to a method for collecting, isolating and amplifying cf-mtDNA from a plasma-derived cfDNA sample. The method comprises the following steps:

A blood sample was obtained from a by drawing blood into a CELL-FREE DNA BCT® (Streck Inc.) blood draw sample tube. The sample tube was inverted about 10 times in order to mix contents and kept at about 4° C. until processing. The sample tube was processed within about 24 hours to maintain viability of sample. The sample tube was centrifuged at about 1900×G for about 15 minutes at about 4° C. using a balanced centrifuge. The sample tube was transferred to a fume hood where the supernatant plasma was removed and transferred into 2 mL EPPENDORF LOBIND® microcentrifuge tubes (EPPENDORF LOBIND is a registered trademark of Eppendorf AG Aktiengesellschaft, Hamburg, Federal Republic of Germany). Care was taken to avoid disturbing the buffy coat of white blood cells within the microcentrifuge sample tubes. The microcentrifuge tubes containing the plasma samples were then centrifuged at about 13,000 RPM for about 15 minutes at about 4° C. using a balanced centrifuge. The supernatant contained the processed cfDNA plasma sample which was then transferred into new 2 mL EPPENDORF LOBIND® microcentrifuge tubes for storage at about −80° C. until further use.

Frozen cfDNA plasma sample were brought to room temperature (RT). The following steps were adapted from the QIAAMP® Circulating Nucleic Acid Handbook (available from Qiagen Gmbh Corporation, Hilden Federal Republic of Germany), which is incorporated by reference herein in its entirety. Briefly, add about 1.6 mL of Buffer ACL to a Falcon 50 mL conical centrifuge tube. Add about 5.6 µL of carrier RNA, from stock prepared according to the manufacturer's instructions, to Falcon tube from the previous step. Add about 1.5 mL of cfDNA plasma sample and about 500 µL phosphate buffered saline (PBS) to the Falcon tube in the first step. Add about 200 µL of Qiagen Proteinase K to the Falcon tube. Close cap of the Falcon tube and mix solution by pulse-vortexing for about 30 seconds. Incubate the Falcon tube at about 60° C. for about 30 minutes using a water bath. Put the Falcon tube in a tube rack and unscrew cap. Add about 3.6 mL of Buffer ACB to the lysed sample, close cap and mix by pulse-vortexing for about 30 seconds. Incubate the solution on ice for about 5 minutes. Prepare QIAvac 24 Plus apparatus as per manufacturer's instructions. Ensure adequate vacuum pressure prior to adding sample(s) to QIAamp Mini column(s). QIAAMP® Mini columns must be kept at about 4° C. until use for optimal isolation efficiency. Apply the incubated solution into the tube extender of the QIAamp Mini column. Switch on the vacuum pump after all solutions (if isolating multiple samples at once) have been applied to their respective tube extender of the QIAAMP® Mini column. Turn off the vacuum pump once all solutions (if isolating multiple samples at once) have been drawn through their respective QIAAMP® Mini column. Release vacuum pressure to 0 mbar. Remove and discard the tube extender(s). Add about 600 µL of Buffer ACW1 to each QIAAMP® Mini column and switch on the vacuum pump. Ensure the cap to QIAAMP® Mini column(s) stays open during vacuum step. Turn off the vacuum pump once all of Buffer ACW1 (if isolating multiple samples at once) has been drawn through their respective QIAAMP® Mini column(s). Release the vacuum pressure to 0 mbar. Apply about 750 µL of Buffer ACW2 to each QIAAMP® Mini column and switch on the vacuum pump. Ensure the cap to QIAAMP® Mini column(s) stays open during vacuum step. Turn off the vacuum pump once all of Buffer ACW1 (if isolating multiple samples at once) has been drawn through their respective QIAAMP® Mini column(s). Release vacuum pressure to 0 mbar. Apply about 750 µL of about 100% ethanol to each QIAAMP® Mini column and switch on the vacuum pump. Ensure the cap to QIAAMP® Mini column(s) stays open during the vacuum step. Turn off the vacuum pump once all of Buffer ACW1 (if isolating multiple samples at once) has been drawn through their respective QIAAMP® Mini column(s). Release vacuum pressure to 0 mbar. Close the lid(s) to QIAAMP® Mini column(s). Remove the QIAAMP® Mini column(s) from QIAvac 24 Plus apparatus and place in a new 2 mL collection tube. Centrifuge the column-tube assembly at about 13,000 RPM for about 5 minutes at RT. Remove the QIAAMP® Mini column(s) and place into a new 2 mL collection tube and incubate the column-tube assembly at about 56° C. for about 10 minutes with the lid open. Remove the QIAAMP® Mini column(s) and place into a 2 mL Eppendorf RNA/DNA LoBind microcentrifuge tube. Apply about 100 µL of UltraPure DNase/RNase-Free Distilled Water (Invitrogen) to the center of the QIAAMP® Mini membrane. Close the lid and incubate for about 10 minutes at RT. Centrifuge the column-tube assembly at about 13,000 RPM for about 3 minutes at RT. Open the lid and apply about 100 µL of UltraPure DNase/RNase-Free Distilled Water (Invitrogen) to the center of the QIAAMP® Mini membrane. Close the lid and incubate for about 10 minutes at RT. Centrifuge the column-tube assembly at about 13,000 RPM for about 3 minutes at RT. Discard QIAAMP® Mini column(s) and store the isolated cfDNA samples at about −80° C. until further use.

The frozen cfDNA plasma samples were brought to RT. The following steps were adapted from the QUBIT® 2.0 Fluorometer manual (available from Invitrogen), which is incorporated by reference herein in its entirety. Briefly, prepare a working solution (about 1 µL High Sensitivity Dye: about 200 µL QUBIT® Buffer per sample being measured). Mix the working solution by pulse-vortexing for about 30 seconds. Add about 5 µL of each cfDNA sample being measured to a separate volume of about 195 µL of working solution. Mix each sample by pulse-vortexing for about 30 seconds. Incubate the samples for about 2 minutes and about 30 seconds at RT. Measure the DNA content of cfDNA samples using manufacturer's instructions for QUBIT® 2.0 fluorometer. If cfDNA samples read between about 0.1 and about 0.3 ng/µL of DNA then proceed to PCR reaction. If sample(s) read lower or higher than this threshold range it is recommended that the cfDNA isolation procedure is re-attempted, ensuring that adequate vacuum pressure is achieved. A concentration-response curve was generated to determine if the starting plasma volume impacted the final cfDNA isolated (see FIG. 2). Store the cfDNA product at about −80° C. until further use.

The frozen cfDNA plasma samples were brought to RT. The following steps were performed to amplify the mtDNA within the cfDNA samples that were derived from subject plasma. Obtain required PCR primers (as described in Table 1 above) and PCR reagents, as provided in Tables 2 and 3 below.

TABLE 2

Reagents required for PCR reaction of the MTL1 primer pair.

| Reagent | Quantity/Reaction (μL) |
|---|---|
| DNA (100-500 pg/μL) | 5.0 |
| MTL1 Forward Primer (10 μM) | 1.0 |
| MTL1 Reverse Primer (10 μM) | 1.0 |
| dNTPs (4 × 2.5 mM) | 4.0 |
| 10X LA-Taq Buffer II (Takara) | 2.5 |
| HS LA Taq Polymerase (Takara) | 0.25 |
| $H_2O$ | 11.3 |
| Total Volume | 25.0 |

TABLE 3

Reagents required for PCR reaction of the MTL2 primer pair.

| Reagent | Quantity/Reaction (μL) |
|---|---|
| DNA (100-500 pg/μL) | 5.0 |
| MTL2 Forward Primer (10 μM) | 1.0 |
| MTL2 Reverse Primer (10 μM) | 1.0 |
| dNTPs (4 × 2.5 mM) | 4.0 |
| 10X LA-Taq Buffer II (Takara) | 2.5 |
| HS LA Taq Polymerase (Takara) | 0.25 |
| $H_2O$ | 11.3 |
| Total Volume | 25.0 |

Follow the recipes provided in Tables 2 and 3. Prepare each cfDNA sample for two PCR reactions. One reaction uses MTL1 primers (a 9239 base pair product) the other reaction uses MTL2 primers (a 11216 base pair product). Once cfDNA and all PCR reagents are added to the PCR plate/tube(s) put caps on and briefly centrifuge at about 700 RPM for about 10 seconds. Load PCR plate/tube(s) onto a PCR thermocycler and run using specifications listed in Table 4 below.

TABLE 4

Description of the PCR reaction conditions for both MTL1 and MTL2 PCR reactions.

94° C. × 5 min
[98° C. × 15 sec, 68° C. × 10 sec, slow ramp to 60° C. × 15 sec,
68° C. × 11 min] × 30 cycles
72° C. × 10 min
4° C. × forever The PCR reactions take approximately 6.5 hours. Store PCR products at about 4° C. until further use.

PCR products from the MTL1 and MTL2 primer reactions were brought to RT and separated on a 2% agarose gel according to a method that comprises the following steps. Add about 1.6 g of laboratory grade agarose to an Erlenmeyer flask containing a stir bar. Add about 80 mL of 1×TAE Buffer to flask. Heat agarose solution in a microwave on high for about 1 minute, remove and swirl contents before microwaving again for about 30 more seconds. Place Erlenmeyer flask into a RT water bath atop a magnetic stir platform. Stir agarose solution for about 5 minutes at about 70% maximum. During about 5 minute stir period, add about 8 μL ethidium bromide. Prepare gel tray for setting of gel and gel electrophoresis apparatus. After about 5 minutes, pour agarose gel solution into a gel tray with lane comb and let polymerize for about 10 minutes. Prepare running buffer. Prepare samples for addition to wells of gel. Into new PCR tubes, add about 2 μL of Orange G loading dye for each sample being run on the gel. Add about 2 μL of MTL1 or MTL2 PCR product as sample. Place caps on samples and briefly spin down at about 700 RPM for about 10 seconds. After about 10 minutes, place polymerized gel into gel electrophoresis apparatus and add running buffer until gel is completely submerged. Retrieve 5 kB or 1 kB molecular weight marker to act as standard. Add about 3 μL of molecular weight marker to far left well of gel. Remove caps from prepared samples and add about 4 μL of Orange G/PCR product mixture to separate wells of the gel, moving one to the right of the molecular weight marker each subsequent addition. Close gel electrophoresis apparatus and connect to power source. Run gel at 160 V for about 2.5 hours. Remove gel from apparatus and proceed to ultraviolet (UV) imaging apparatus.

Figure 2:
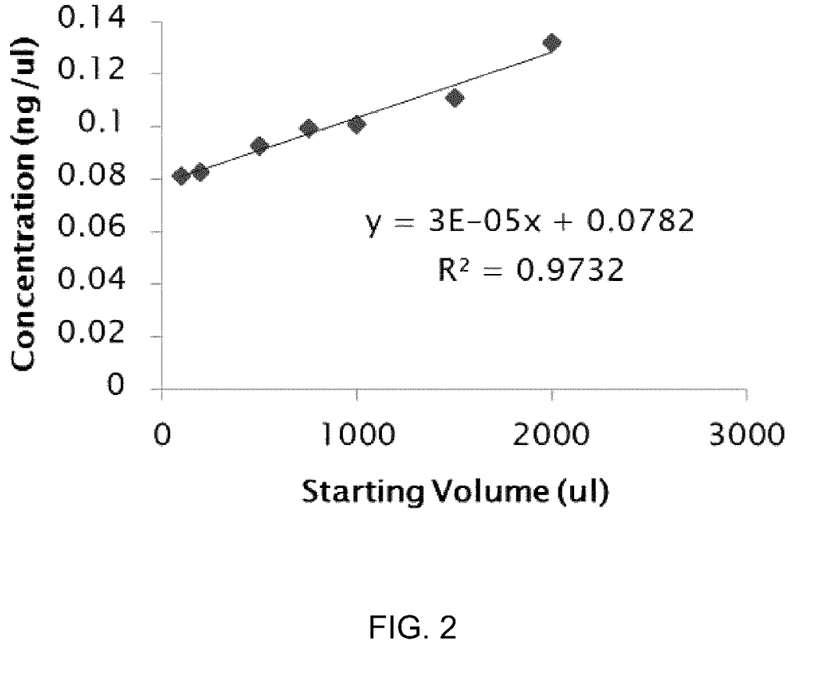
FIG. 2 is a line graph that shows an example of a correlation analysis between a starting volume of plasma and the concentration of cfDNA within seven plasma samples taken from the same subject, but of various initial volumes.
Figure 3:
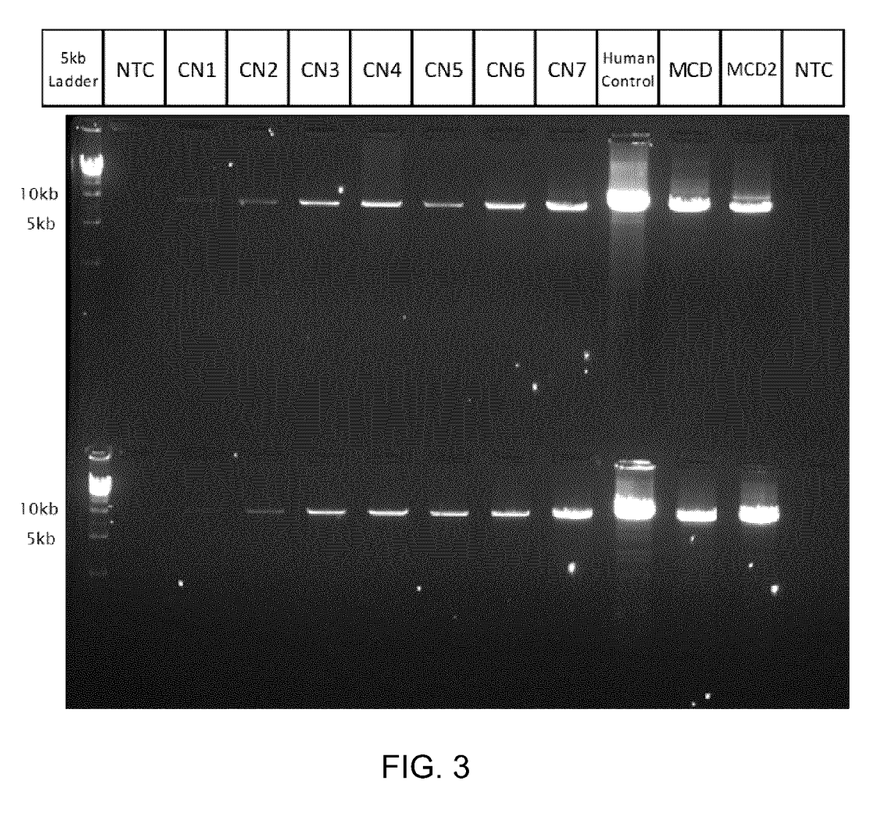
FIG. 3 is an image of an example agarose gel used to separate mtDNA that was amplified from cfDNA plasma samples using a first PCR primer and a second PCR primer.
Figure 4:
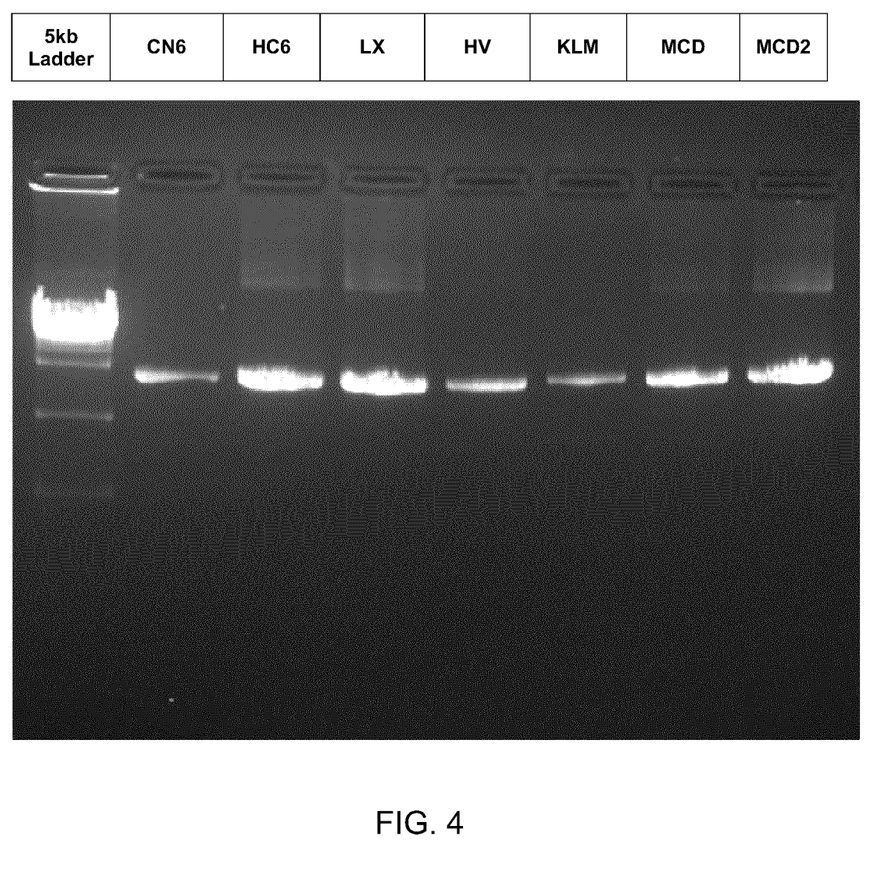
FIG. 4 is an image of an example agarose gel used to separate mtDNA that was amplified from cfDNA plasma samples using the first PCR primer pair.
Figure 5:
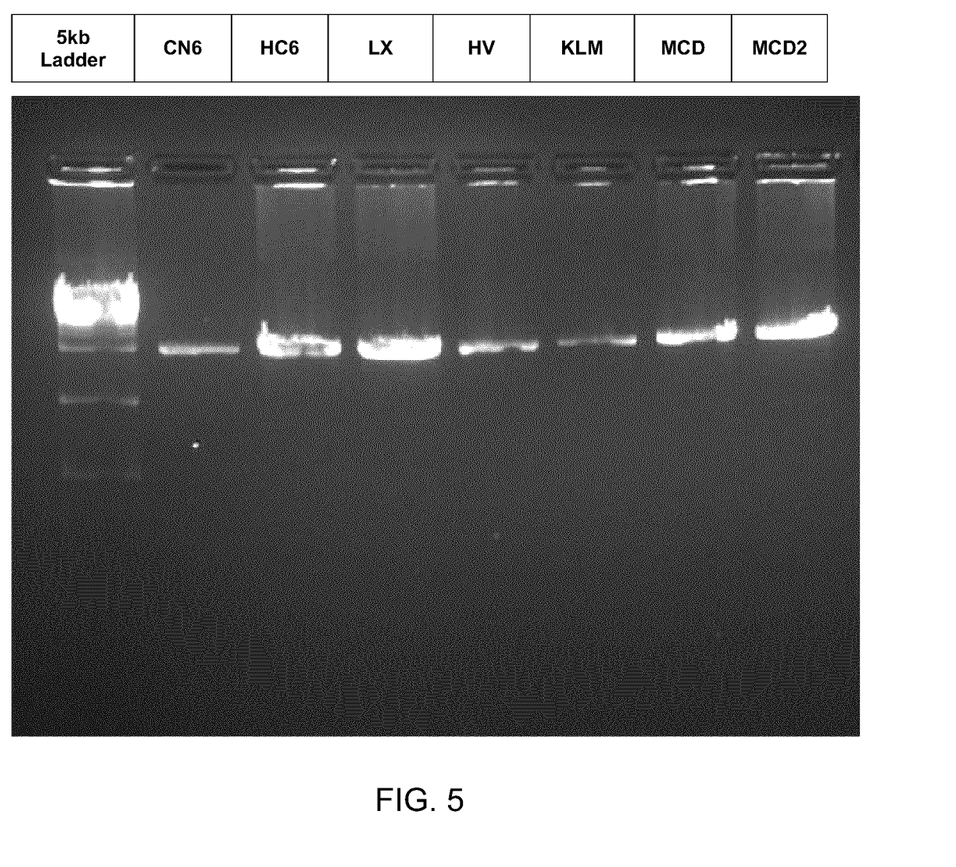
FIG. 5 is an image of an example agarose gel used to separate mtDNA that was amplified from cfDNA plasma samples using the second PCR primer pair.

Following UV imaging, detection of the two overlapping mitochondrial DNA fragments comprising the full circular mitochondrial genome can be identified at their respective sizes of 9239 bp for MTL1 and 11216 bp for MTL2 (see FIG. 3, FIG. 4 and FIG. 5). As described further in Example 2 below, a concentration-response curve was generated to determine if that starting plasma volume impacted the final cfDNA that was isolated (see FIG. 2).

The cfDNA samples were sequenced according to protocols used by the University of Calgary Core DNA Services and comprised the following steps. About 100 μL of isolated cfDNA was provided per sample for sequencing. Samples were prepared using the NEBNEXT® Ultra II DNA Library Prep Kit for Illumina. About 20 ng of DNA were used for this stage as determined following DNA quantification using the QUBIT® 2.0 fluorometer. Indexed libraries were pooled and sequenced using a MiSeq desktop sequencing instrument (see www.illumina.com, the disclosure of which is incorporated herein by reference). Each sequencing run was paired end 2×75 bp using a v3 150 cycle MiSeq cartridge (see www.illumina.com, the disclosure of which is incorporated herein by reference). Output was generated into BAM files for bioinformatics analysis. Sequencing data was run through the free open source HaploGrep v2.0 software (haplogroup.uibk.ac.at, the disclosure of which is incorporated herein by reference) to determine patient haplogroup. Results were compared against patient haplogroup data generated clinically using muscle biopsy tissue collected and reported as part of clinical diagnosis of patient mitochondrial disease. Confirmation of haplogroup using both cfDNA and muscle was performed, thus confirming the utility of cfDNA to identify mtDNA mutations.

Table 5 provides data that confirms the cfDNA samples to muscle biopsies obtained.

TABLE 5

Analyzed output of haplogroup confirmation when comparing cfDNA to muscle biopsies using HaploGrep v2.0 software.

| Sample ID | Muscle Haplogroup | cfDNA Haplogroup |
|---|---|---|
| MCD | H1a(H1a3c) | H1a(H1a3c) |
| ML | T2b(T2b5) | T2b(T2b5) |

Example 2

Due to the very small quantities of isolated cfDNA from each plasma sample, the inventors performed this analysis to substantiate how successful the cfDNA isolation was. To test this approach the inventors used samples from the same individual and altered the amount of starting plasma to produce seven samples CN 1 through CN7 of differing levels of cfDNA, as provided in Table 6.

TABLE 6

The starting volumes of plasma (µL) of seven plasma samples and the concentration of cfDNA detected in each sample.

| Sample ID | Concentration (ng/ul) | Starting Plasma |
|---|---|---|
| CN1 (100 ul) | 0.0812 | 100 |
| CN2 (200 ul) | 0.0824 | 200 |
| CN3 (500 ul) | 0.0924 | 500 |
| CN4 (750 ul) | 0.0992 | 750 |
| CN5 (1000 ul) | 0.101 | 1000 |
| CN6 (1500 ul) | 0.111 | 1500 |
| CN7 (2000 ul) | 0.132 | 2000 |

FIG. 2 shows the correlation between the starting volume of plasma and the concentration of cfDNA. The inventors observed a linear response that correlated to the amount of starting plasma with the QUBIT® 2.0 reading.

Example 3

Another embodiment of the present disclosure relates to a diagnostic tool. Cf-mtDNA can be used to detect mutations in mtDNA that are sourced from a wider variety of organs than standard peripheral leukocyte methods. For example, organs such as the liver, heart, kidneys and skeletal muscle could release mtDNA into a subject's circulatory system that would be captured in the cell-free fraction. This may allow detection of mutations in mtDNA that is representative of most or all of a subject's cells.

Example 4

Another embodiment of the present disclosure relates to a detection tool or method for detecting "mitochondrial transfer" during cell therapies. For example, a mesenchymal stem cell infusion (MSC) can transfer mitochondria to recipients without engraftment. Typically, once this process has occurred the only way to detect changes in the mtDNA content in the recipient is with tissue biopsy to examine citrate synthase activity or to look at mtDNA content in tissues. This would not likely be feasible in patients who undergo this procedure to treat their underlying mitochondrial disease. Cf-mtDNA could detect donor MSC mtDNA and thereby determine whether there was mtDNA transfer from MSC infusions. The inventors have applied this technology in liver cell transplant for urea cycle disorders and were able to detect donor cf-nuclear DNA close to 6 months after cell engraftment had taken place. Autologous donor liver cells were genotyped using multiple markers in nuclear DNA and cf-nuclear DNA in the recipient was also genotyped in a similar manner. Liver cells were given as hourly infusions for 6 consecutive days. The cf-nuclear DNA content of donor cells was determined at baseline (prior to giving the cells), at 1 week, 4 weeks and 26 weeks post baseline. The results showed a stepwise reduction in cf-nuclear donor DNA from 0.075% to 0.015% over 26 weeks. However, given that the half life of cf-nuclear DNA is short (median half-life 16.3 minutes), one explanation for any donor cf-nuclear DNA to be present at 26 weeks is that the donor liver cells engrafted. The decline in cf-nuclear DNA is expected because shortly after the liver cell infusion is completed, there would be a high cf-nuclear DNA content from dead cells that would initially convert to the source being engrafted cells.

The invention claimed is:

1. A method for identifying a mitochondrial DNA deletion mutation in an individual, the method comprising: isolating cell-free DNA from a sample obtained from the individual; amplifying the cell-free DNA to generate at least two amplification products of mitochondrial DNA from the cell-free DNA using at least two pairs of primers which hybridize to selected segments of a human mitochondrial DNA genome, wherein the at least two pairs of primers comprise at least a first primer pair consisting of SEQ ID NO: 1 and 2 and at least a second primer pair consisting of SEQ ID NO: 3 and 4, wherein the at least two or more amplification products generated overlap with each other and represent the entire mitochondrial DNA genome of the individual; and identifying the mitochondrial DNA deletion mutation by analyzing the amplification products in the mitochondrial DNA relative to a reference human mitochondrial DNA genome.

2. The method of claim 1, wherein the at least two pairs of primers each generate an amplification product representing at least about 55% of the human mitochondrial DNA genome.

3. The method of claim 1, wherein the sample is a blood plasma sample.

4. The method of claim 1, wherein the analyzing of the amplification products is performed by sequencing of the amplification products.

5. The method of claim 1, wherein the step of analyzing the amplification products comprises comparing sequences of the amplification products with mitochondrial DNA sequences obtained from tissue biopsies of a plurality of individuals.

6. The method of claim 5, wherein the mitochondrial DNA sequences obtained from the tissue biopsies are stored in a database, wherein each of the mitochondrial DNA sequences is associated with a haplogroup.

7. The method of claim 6, wherein the tissue biopsies are muscle biopsies.

8. A method for detecting mitochondrial DNA transfer, the method comprising the steps of: a) obtaining a plasma sample from a subject that has received a mesenchymal stem cell infusion from a donor; b) isolating cell-free DNA from-the plasma sample; c) amplifying the cell-free DNA to generate at least two amplification products of mitochondrial DNA from the cell-free DNA using two or more pairs of primers which hybridize to selected segments of a reference human mitochondrial DNA genome wherein the two or more primer pairs comprise a first primer pair consisting of SEQ ID NO: 1 and 2 and a second primer pair consisting of SEQ ID NO: 3 and 4, wherein the two or more amplification products generated overlap with each other and will represent the entire mitochondrial DNA genome of the subject and the donor: and d) analyzing the amplification products to determine if the mitochondrial DNA genome of the donor is present.

9. The method of claim 8, wherein the at least two pairs of primers each generate an amplification product representing at least about 55% of the human mitochondrial DNA genome.

10. The method of claim 8, wherein the sample is a blood plasma sample.

11. The method of claim 8, wherein the analyzing of the amplification products is performed by sequencing of the amplification products.

12. The method of claim 8, wherein the step of analyzing the amplification products comprises comparing sequences of the amplification products with the mitochondrial DNA genome obtained from a tissue biopsy of the donor.

13. The method of claim 12, wherein the tissue biopsy is a muscle biopsy.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Forward Primer "MTL1"

<400> SEQUENCE: 1
aaagcacata ccaaggccac                                              20

<210> SEQ ID NO 2
<211> LENGTH: 22
<212> TYPE: DNA
<213> ORGANISM: Artificial Sequence
<220> FEATURE:
<223> OTHER INFORMATION: Reverse Primer "MTL1"

<400> SEQUENCE: 2
ggttctgtgg gcaaatttaa ag                                           22

<210> SEQ ID NO 3
<211> LENGTH: 22
<212> TYPE: DNA
<213> ORGANISM: Artificial Sequence
<220> FEATURE:
<223> OTHER INFORMATION: Forward Primer "MTL2"

<400> SEQUENCE: 3
```

```
tgaggccaaa tatcattctg ag                                                22

<210> SEQ ID NO 4
<211> LENGTH: 20
<212> TYPE: DNA
<213> ORGANISM: Artificial Sequence
<220> FEATURE:
<223> OTHER INFORMATION: Reverse Primer "MTL2"

<400> SEQUENCE: 4
aatgttgagc cgtagatgcc                                                   20
```